US012808837B2

(12) United States Patent
Sammes et al.

(10) Patent No.: US 12,808,837 B2
(45) Date of Patent: Nov. 24, 2026

(54) HYDROGEN SENSOR FOR ALUMINUM-WATER REACTIONS

(71) Applicant: Clean Water Ventures, Inc., Reno, NV (US)

(72) Inventors: Lauren Sammes, Reno, NV (US); Brian Sheetz, Reno, NV (US)

( * ) Notice: Subject to any disclaimer, the term of this patent is extended or adjusted under 35 U.S.C. 154(b) by 124 days.

(21) Appl. No.: 18/767,790

(22) Filed: Jul. 9, 2024

(65) Prior Publication Data

US 2026/0016441 A1 Jan. 15, 2026

(51) Int. Cl.
*G01N 27/407* (2006.01)
*G01N 27/406* (2006.01)
*G01N 33/00* (2006.01)

(52) U.S. Cl.
CPC ..... *G01N 27/4074* (2013.01); *G01N 27/4062* (2013.01); *G01N 27/4065* (2013.01); *G01N 33/0027* (2013.01)

(58) Field of Classification Search
CPC ........... G01N 27/4074; G01N 27/4062; G01N 27/4065; G01N 27/4073; G01N 33/0027; G01N 33/0005
See application file for complete search history.

(56) References Cited

U.S. PATENT DOCUMENTS 3,932,600 A * 1/1976 Gutbier .................... C01B 3/061 422/111
4,907,440 A * 3/1990 Martin ............... G01N 33/2025 73/19.07

OTHER PUBLICATIONS

Fukatsu, N., Kurita, N. Hydrogen sensor based on oxide proton conductors and its application to metallurgical engineering. Ionics 11, 54-65 (2005) (Year: 2005).*

(Continued)

*Primary Examiner* — Alexander S Noguerola
(74) *Attorney, Agent, or Firm* — Jaquez Land Greenhaus & McFarland, LLP; Bruce W. Greenhaus

(57) ABSTRACT

Various embodiments of a method and apparatus for sensing hydrogen produced continually by a reaction between aluminum and water are disclosed. The hydrogen sensor includes a proton-carrying electrolyte, an RE (reference electrode) lining a first side of the proton-carrying electrolyte, an SE (sensor electrode) lining a second side of the proton-carrying electrolyte, and a voltage-measuring device electrically connected to the RE and the SE to measure a voltage drop across the electrolyte. The proton-conducting electrolyte is capable of maintaining a gradient of concentration of protons between the SE and the RE at 250° C. In some embodiments, the proton-carrying electrolyte is a barium-zirconate-cerate material doped with yttrium (BCZY). In some embodiments, the RE and the SE are made from platinum. In some embodiments, the electrolyte has a conical shape and is placed on one end of a ceramic vessel with the SE on the exterior of the hydrogen center.

20 Claims, 6 Drawing Sheets

(56) References Cited

OTHER PUBLICATIONS

"REE—Rare Earth Elements and their Uses" article at https://geology.com/articles/rare-earth-elements, presumed published 2026 (Year: 2026).*
Hinojo, A.; Lujan, E.; Nel-lo, M.; Abella, J.; Colominas, S. Potentiometric Hydrogen Sensor with 3D-Printed BaCe0.6Zr0.3Y0.1O3-Electrolyte for High-Temperature Applications. Sensors 2022, 22, 9707 (Year: 2022).*
PalmSens EmStat3 series Brochure, Rev. Nov. 2018 (Year: 2018).*
Islam et al., "Proton Migration and Defect Interactions in the CaZrO3 Orthorhombic Perovskite: A Quantum Mechanical Study," Chem. Mater. 2001, 13, 2049-2055 (Year: 2001).*

* cited by examiner

HYDROGEN SENSOR FOR ALUMINUM-WATER REACTIONS

BACKGROUND

(1) Technical Field

The disclosed method and apparatus relate generally to systems for measuring concentrations of hydrogen. In particular, the disclosed method and apparatus relate to measuring the concentration of hydrogen generated by a reaction of aluminum and water at pH 7 to basic conditions (for example in a KOH or NaOH solution).

(2) Background

Hydrogen can be generated from a reaction of aluminum and water. However, measuring the amount of hydrogen being produced can be problematic due at least in-part to the difficulties of removing the gas continually.

Accordingly, providing a system that can measure hydrogen concentrations instantaneously, without removing the hydrogen from the flow, would be advantageous.

SUMMARY

Various embodiments of a method and apparatus for a hydrogen sensor are disclosed.

In some embodiments, the hydrogen sensor uses a proton-conducting solid electrolyte. In some embodiments, the electrolyte is based on A and B-sites having the form of the perovskite $ABO_3$. In some embodiments, the A site includes Ba and the B site includes Ce and Zr forming $BaCeO_3$ and $BaZrO_3$, respectively. In some embodiments, the proton-conducting solid electrolyte is sandwiched between an RE (reference electrode) and an SE (sensing electrode), forming an electrode-electrolyte-electrode cell. The different partial pressures are associated with different chemical potentials at the RE and the SE, which generate an electrical potential difference between the RE and the SE. However, in some embodiments, the electrodes are electronically conductive, porous and electrocatalytically active. A difference in chemical potential generates a gradient of protons between the RE and the SE. In some embodiments, the SE and the RE are metals, and the combination of SE-electrolyte-RE forms a metal-electrolyte-metal cell. In some embodiments, the metal-electrolyte-metal cell is of the type (Pt|BCZY|Pt), where Pt (platinum) is used as the RE and the SE, and the electrolyte is a mixed barium-zirconate-cerate material (BCZY), doped with Y (as indicated by the "Y" in BCZY). In some embodiments, the shape of the cell is a cone. The cone is attached to one end of a ceramic conduit. In some embodiments, the ceramic conduit is made from alumina.

The shape of the tip of the hydrogen sensor allows for easier insertion into the reactor. The reference electrode is an inlet of hydrogen at a standard, partial pressure, and thus standard concentration. Wires are then connected through a meter, and the potential difference, the OCV (open circuit voltage), is then measured with the SE measuring the partial pressure of the hydrogen in the reactor continuously.

The use of the proton-carrying electrolyte allows the hydrogen sensor to be used in a hydrogen reactor that produces hydrogen from a chemical reaction. The OCV can be measured continuously, allowing the hydrogen concentration to be measured in situ.

The EMF (electromotive force) associated with the voltage drop in the electrolyte, which is the OCV, can be calculated by the equation:

$$E = -\frac{RT}{2F}\ln\left(\frac{P'_{H2}}{P''_{H2}}\right), \quad \text{(equation 1)}$$

where the R is the ideal gas constant (which is also the universal gas constant), the F is Faraday's constant, the T is the absolute temperature, the $P'_{H2}$ and the $P''_{H2}$ are the hydrogen partial pressures at the SE and the RE, respectively, ($P'_{H2}$ is the standard partial pressure) and the E is the OCV between the SE and the RE. Note that the ratio of the universal ideal gas constant to Faraday's constant is the same as the ratio of Boltzmann's constant to the charge of an electron.

Inverting the above equation one obtains, $$P'_{H2} = P''_{H2}e^{\frac{-2FE}{RT}}. \quad \text{(equation 2)}$$

Thus, given the E, the T and the $P''_{H2}$, the $P'_{H2}$ can be computed. Since the hydrogen partial pressure, $P''_{H2}$ in the reference atmosphere and the temperature are known, the hydrogen concentration of interest, $P'_{H2}$, can be determined by measuring the OCV, E.

In various embodiments, a hydrogen sensor comprises (1) a proton-conducting electrolyte, (2) an RE lining a first side of the proton-conducting electrolyte, (3) an SE lining a second side of the proton-conducting electrolyte and (4) a voltage measuring device that is electrically connected to the RE and the SE to measure a voltage drop between the RE and the SE. The proton-carrying electrolyte is capable of maintaining a gradient of concentration of hydrogen cations between the SE and the RE at between 250° C.-450° C.

In various embodiments, a method comprises: (1) receiving at an RE a charge proportional to a partial pressure of hydrogen in a reference gas, the RE lining a first side of a proton-carrying electrolyte, (2) receiving at an SE a charge proportional to a hydrogen partial pressure in a reaction, the SE lining a second side of the proton-carrying electrolyte, and (3) maintaining a gradient of proton concentration in the proton-carrying electrolyte and (4) measuring a voltage with a voltage measuring device that is electrically connected to the RE and the SE to measure a voltage drop between the RE and the SE. The proton-carrying electrolyte is capable of maintaining a gradient of concentration of hydrogen cations between the SE and the RE at 250° C.

In various embodiments, a method comprises (1) transporting, by one or more reaction-chamber inlet conduits, starting materials for a reaction, into the reaction chamber, where the starting materials include aluminum and water, (2) transporting, by one or more outlet conduits, an end product out of the reaction chamber, the end product includes hydrogen; the reaction chamber includes a port for accepting a hydrogen sensor. The hydrogen sensor includes an electrolyte of barium-zirconate-cerate material doped with yttrium (BCZY), the electrolyte having a conical shape; wherein (1) the conical shape has an exterior side covered with a platinum SE and (2) the conical shape has an interior side covered with a platinum RE. The method further comprises carrying a reference gas, by a reference gas inlet, to the interior side of the conical shape, causing the reference gas to come in contact with the platinum RE. The hydrogen sensor is located in a port of the system with the platinum SE being oriented to face gas from the reaction chamber. The method further comprises (1) allowing gas from the reaction chamber to contact the platinum SE and (2) generating a voltage drop from a ratio of a hydrogen partial pressure of the gas from the reaction chamber and a hydrogen partial pressure of the reference gas, where the voltage drop is between the platinum SE and the platinum RE. In various embodiments, the method further comprises (1) sensing a hydrogen concentration in a reaction chamber by the hydrogen sensor by sensing the voltage drop between the platinum RE and the platinum SE and (2) communicating the voltage drop between the platinum RE and the platinum SE to an output.

In various embodiments, a method of assembling a hydrogen sensor. The method comprises (1) forming a proton-conducting electrolyte, (a) lining a first side of the proton-conducting electrolyte with an RE and (b) lining a second side of the proton-conducting electrolyte with an SE and (2) electrically attaching a voltage measuring device to the RE and the SE to allow a voltage drop between the RE and the SE to be measured. The proton-conducting electrolyte is capable of maintaining a gradient of concentration of protons between the SE and the RE at 250° C.-450° C. In some embodiments, the temperature can be as low as 100° C. In some embodiments, the temperature can be as high as 550° C. In some embodiments, the temperature should be high enough so that the hydrogen is gaseous and contacts the hydrogen sensor. In some embodiments, the temperature should be low enough so that hydrogen at the electrolyte remains in contact with the electrolyte.

In various embodiments, a method comprises building a reaction chamber including connecting one or more inlet conduits to the reaction chamber, the one or more inlet conduits being capable of transporting starting materials into the reaction chamber. The starting materials include aluminum and water or a basic solution of KOH or NaOH. The building of the reaction chamber also includes connecting one or more one or more outlet conduits to the reaction chamber, the one or more outlet conduits being capable of transporting an end product out of the reaction chamber. The end product includes hydrogen. The building of the reaction chamber includes forming a port for accepting a hydrogen sensor in the reaction chamber. The method further comprises building the hydrogen sensor by forming an electrolyte having a barium-zirconate-cerate material doped with yttrium dopant (BCZY), the electrolyte having a conical shape. The conical shape has an exterior side and an interior side. The building of the hydrogen sensor also includes (1) covering the exterior side of the conical shape with a platinum SE (2) covering the interior side of the conical shape with a platinum RE and (3) connecting a gas inlet to carry a reference gas to the interior side of the conical shape, to cause the reference gas to come in contact with the platinum RE.

In various embodiments, the method further comprises placing the hydrogen sensor into a port of the system, so that (a) the platinum SE is oriented to face gas from the reaction chamber and (b) a ratio of a hydrogen partial pressure of the gas from the reaction chamber and a hydrogen partial pressure of the reference gas generates a voltage drop between the platinum SE and the platinum RE. The method further comprises connecting the platinum SE and the platinum RE to an output.

In various embodiments, a system comprises a reaction chamber, where the reaction chamber includes (1) one or more inlet conduits for transporting starting materials into the reaction chamber, the starting materials including aluminum and water, (2) one or more outlet conduits for transporting an end product out of the reaction chamber. The end product includes hydrogen. The system further comprises a port for accepting a hydrogen sensor. The system further comprises a hydrogen sensor. The hydrogen sensor includes an electrolyte that has a barium-zirconate-cerate material doped with yttrium (BCZY). The electrolyte has a conical shape. The conical shape has an exterior side covered with a platinum SE and (2) the conical shape has an interior side covered with a platinum RE. The hydrogen sensor is located in the port of the system with the platinum SE and is oriented to face gas from the reaction chamber so that a ratio of a hydrogen partial pressure of the gas from the reaction chamber and a hydrogen partial pressure of the reference gas generates a voltage drop between the platinum SE and the platinum RE. The platinum SE and the platinum RE are in electrical contact with an output. The gas inlet carries a reference gas to the interior side of the conical shape, causing the reference gas to come in contact with the platinum RE.

In various embodiments, the proton-conducting electrolyte comprises a perovskite doped with a rare earth element. In various embodiments, the perovskite includes an A cation and a B cation in a structure $ABO_3$, where the A cation is selected from any of Ca, Ba, Sr, La and K, and the B cation is selected from any of Ce, Zr, Ta and Nb. In various embodiments, the A cation is a 12-coordinated $A^{2+}$ cation, and the B cation is a 6-coordinated $B^{4+}$ cation. In various embodiments, both the A cation and the B cation are doped. In various embodiments, the rare earth element is selected from any of Y, Yb, In, Sc, Gd, Nd, Sm, Ga, Er or combinations, thereof. In various embodiments, the proton-carrying electrolyte is a barium-zirconate-cerate material doped with yttrium (BCZY). In various embodiments, the hydrogen sensor further comprises a first platinum wire connecting the RE to the voltage measuring device and a second platinum wire connecting the SE to the voltage measuring device. In various embodiments, the voltage-measuring device comprises a multimeter. In various embodiments, the voltage measuring device comprises a controller. In various embodiments, the controller includes one or more machine instructions. When the controller implements the one or more machine instructions, the controller reads the voltage drop and determines whether to take a corrective action based (1) on an equation, $$P'_{H2} = P''_{H2} e^{\frac{-2FE}{RT}},$$

and (2) whether the $P'_{H2}$ or the E is outside of an acceptable range of values, where (1) the $P'_{H2}$ is a partial pressure of hydrogen at the SE, (2) the $P''_{H2}$ is a partial pressure of hydrogen at the RE, (3) the F/R is a value of the F is Faraday's constant divided by an ideal gas' universal constant, and (4) the T is a value of absolute temperature at the RE and (5) the E is the voltage drop between the RE and the SE. In various embodiments, the proton-carrying electrolyte has a conical shape. In various embodiments, the hydrogen sensor further comprises a ceramic vessel, which is connected to the proton-carrying electrolyte. In various embodiments, the hydrogen sensor further comprises a gas inlet which is a conduit connecting a source and a region in contact with the RE, via which a reference gas is transferable from the source to the region in contact with the RE. In various embodiments, the ceramic vessel is connected to the proton-carrying electrolyte so that a cavity is formed by the RE and the ceramic vessel, and the ceramic vessel holds a reference gas. In various embodiments, the proton-carrying electrolyte comprises a barium-zirconate-cerate material doped with yttrium (BCZY). In various embodiments, the platinum SE is located in the reaction chamber.

BRIEF DESCRIPTION OF THE DRAWINGS

The disclosed method and apparatus, in accordance with one or more various embodiments, is described with reference to the following figures. The drawings are provided for purposes of illustration only and merely depict examples of some embodiments of the disclosed method and apparatus. These drawings are provided to facilitate the reader's understanding of the disclosed method and apparatus. They should not be considered to limit the breadth, scope, or applicability of the claimed invention. It should be noted that for clarity and ease of illustration these drawings are not necessarily made to scale.

The figures are not intended to be exhaustive or to limit the claimed invention to the precise form disclosed. It should be understood that the disclosed method and apparatus can be practiced with modification and alteration, and that the invention should be limited only by the claims and the equivalents thereof.

DETAILED DESCRIPTION

A hydrogen sensor is provided that continuously measures the hydrogen partial pressure within a reaction chamber in which hydrogen and energy are generated from water and aluminum.

Figure 1:
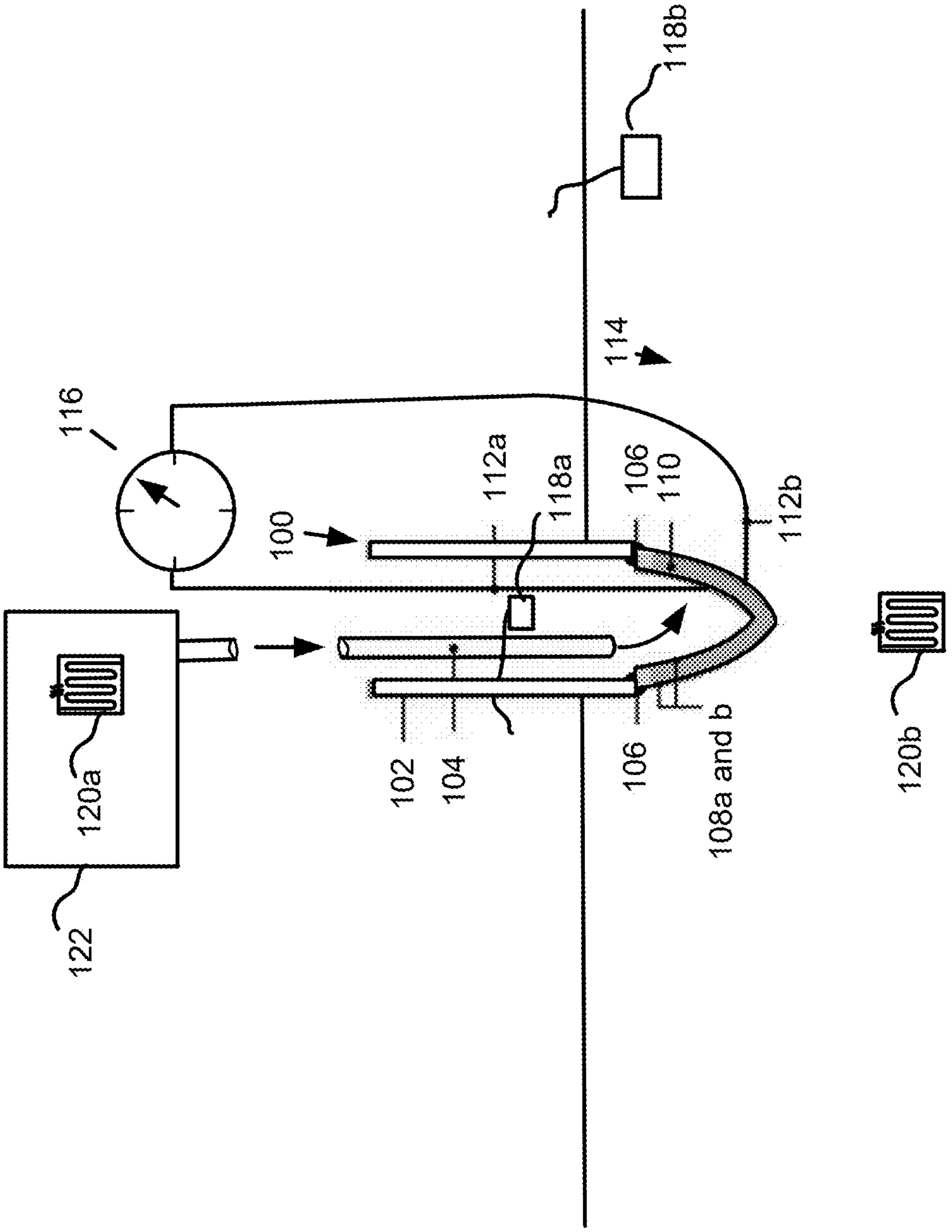
FIG. 1 illustrates various embodiments of a hydrogen sensor, which measures the concentration of hydrogen in a flow and a system in which the hydrogen sensor is deployed.

FIG. 1 illustrates various embodiments of a hydrogen sensor 100, which includes a ceramic vessel 102. In some embodiments, the ceramic vessel 102 is made from aluminum oxide (alumina). In some embodiments, the ceramic vessel 102 is made from stabilized cubic or tetragonal zirconium dioxide (zirconia). In some embodiments, the ceramic vessel 102 is open at two opposite ends, allowing gases to pass from one end to the other end. In some embodiments, the ceramic vessel 102 includes a cavity where gas can collect. In some embodiments, the ceramic vessel 102 is a duct or other conduit. In some embodiments, the ceramic vessel 102 is a tube. In some embodiments, the tube is cylindrical. The ceramic vessel 102 holds a reference gas, which has a known partial pressure due to hydrogen (which is a reference partial pressure). In some embodiments, the reference gas is 5% to 90% hydrogen. In some embodiments, the hydrogen is mixed with one or more inert gases (for safety). In some embodiments, the hydrogen is mixed with nitrogen. In some embodiments, the pressure of the reference gas is 1 atmosphere (e.g., the reference gas and reaction chamber are not pressurized). In some embodiments, the reference gas is introduced into the ceramic vessel 102 by a gas inlet 104. In some embodiments, the gas inlet 104 is a conduit made of a ceramic. In some embodiments, the gas inlet 104 is made from alumina. In some embodiments, the gas inlet 104 is made from zirconia. In some embodiments, the gas inlet 104 is a tube. In some embodiments, the introduction of the gas into the ceramic vessel 102 is performed by pumping the gas. In some embodiments, the reference gas is heated to the same temperature as a reaction chamber 114. In some embodiments, thermal sensors are placed in the ceramic vessel 102 and the reaction chamber 114 to ensure that the temperatures of the reaction chamber 114 and ceramic vessel are the same, within a given tolerance. In some embodiments, the reference gas continually flows. In other embodiments, the gas inlet 104 is replaced by a gas outlet, and by drawing the gas out, by the gas outlet, as the gas is removed from the ceramic vessel 102, a negative pressure is created in ceramic vessel 102 drawing the gas into the ceramic vessel 102 to replace the gas that was removed.

At one end of the ceramic vessel 102 is a tip, which is attached to the ceramic vessel 102 by a binder 106. The binder 106 can be any high-temperature cement or glass cement. An interior of the tip is lined with an RE **108*a*, and an exterior of the tip is lined with an SE 108*b*. The RE 108*a* and the SE 108*b* sandwich an electrolyte 110. During operation, the surface of the hydrogen sensor (and electrolyte 110) upon which the RE 108*a* is deposited contacts the gas within the ceramic vessel 102. The SE 108*b* is placed within the reaction chamber 114. The ratio of the partial pressures of the hydrogen in contact with the RE 108*a* and the SE 108*b* generates an electrical potential difference between the RE 108*a* and the SE 108*b*. In some embodiments, the RE 108*a* and the SE 108*b* are two or three microns to a few hundred microns thick. The electrolyte 110 maintains a potential gradient between the RE 108*a* and the SE 108*b*, generated by the different hydrogen ion concentrations at the RE 108*a* and the SE 108*b*. Since the hydrogen cations are missing an electron, and the hydrogen atoms in the reaction chamber are not, the hydrogen cations in the electrolyte tend to be drawn towards, or attracted to, the reaction chamber. The potential difference is proportional to the natural log of the partial pressure ratio. In some embodiments, the electrolyte 110 is any proton-carrying electrolyte. In some embodiments, the electrolyte 110 is a doped alkaline-earth-metal cerate, zirconate, or cerate-zirconate. In some embodiments, the electrolyte 110 is barium-zirconate-cerate (BCZY) doped with yttrium (Y). In some embodiments, the electrolyte 110 is BCY or BZY. In some embodiments, the hydrogen sensor 100** is capable of operating at 250° C. and above (in contrast to oxygen sensors that require an operating temperature of 500° C. to 600° C.).

In some embodiments, the electrolyte 110 is a high-temperature perovskite proton conductor. In some embodiments, the electrolyte 110 is a high-temperature proton conductor based on a structure of $ABO_3$, which is doped, where A is any of (or combination of) Ca, Ba, Sr, La and K, and B is any of (or combination of) Ce, Zr, Ta and Nb. In some embodiments, the dopant is any material that enhances the electrolyte's ability to carry a proton current or hydrogen cation current. In some embodiments, the dopant is a rare earth element. In some embodiments, the dopant is any of Y, Yb, In, Sc, Gd, Nd, Sm, Ga, Er or combinations, thereof. In some embodiments, both the A-site and the B-site are doped. Dopants of differing radii can be used. Depending on the size of the dopant, the dopant will occupy oxygen sites, producing oxygen vacancies, which are beneficial for conduction. The dopants cannot be so large as to change the material. In some embodiments, the $ABO_3$ perovskite consists of large-sized 12-coordinated $A^{2+}$ cations, while small-sized 6-coordinated $B^{4+}$ cations (regarding the meaning of the terms "large" and "small," the 12-coordinated $A^{2+}$ cations are large compared to the 6-coordinated $B^{4+}$ cations and the 6-coordinated $B^{4+}$ cations are small compared to the 12-coordinated $A^{2+}$ cations). The "6-coordinated" $B^{4+}$ cations are surrounded by 6 ions and the "12-coordinated" $A^{2+}$ cations are surrounded by 12 ions. In some embodiments, the $ABO_3$ perovskite is $SrCeO_3$, $SrZrO_3$, $BaCeO_3$, $BaZrO_3$, $KTaO_3$, $LaNbO_4$. In some embodiments, the ability of hydrogen sensor 100 to detect hydrogen is facilitated by the choice of dopants and reaction conditions favorable to the Al-oxygen reaction. In some embodiments, the elevated temperature (e.g., 250° C. to 450° C.) at which the Al-water reaction occurs facilitates keeping the hydrogen ions near the electrolyte 110 in contact with the electrolyte 110 and thereby facilitates detecting hydrogen.

In some embodiments, the electrolyte 110 is $BaCe_{1-x}M_xO_{3-\delta}$ or $BaZr_{1-x}M_xO_{3-\delta}$, where M is a rare earth element, x is less than its upper limit of solid solution formation range (in some embodiments, x is less than 0.2), and δ is the oxygen deficiency per unit formula. In some embodiments, M is one of Y, Yb, In, Sc, Gd, Nd, Sm, Ga, Er or combinations, thereof.

In some embodiments, the electrolyte 110 is kept thin enough, so that the resistance drop across the electrolyte is low enough so that the electrical signal changes rapidly enough for useful operation at temperatures, which are lower than those required for thicker electrolytes. In some embodiments, the electrolyte is 20 to 50 microns.

Wires 112*a* and *b* are electrically connected to the RE 108*a* and the SE 108*b*, respectively, and to a meter 116 (or another voltage measuring device). Wires 112*a* and *b* carry the voltage to the meter 116 or another device for measuring the potential difference. In some embodiments, the RE 108*a*, the SE 108*b* and the wires 112*a* and *b* are made from platinum. In other embodiments, another highly conductive material that does not react with the contents of the reaction chamber or the contents of the ceramic vessel 102. In some embodiments, the RE 108*a*, the SE 108*b* and the wires 112*a* and *b* are silver. In some embodiments, the RE 108*a*, the SE 108*b* and the wires 112*a* and *b* are gold. In some embodiments, the RE 108*a*, the SE 108*b* and the wires 112*a* and *b* can be palladium, ruthenium, rhodium, iridium, or osmium. In some embodiments, the RE 108*a* and the SE 108*b* can be iron, nickel, copper or cobalt. However, metals that are not likely to oxidize or corrode are preferred over metals that are more likely to oxidize or corrode. In other embodiments, the RE 108*a*, the SE 108*b* and the wires 112*a* and *b* can be any metal or conductive oxide. For example, in some embodiments, the RE 108*a* and the SE 108*b* can be any precious metal or any group III metal. In some embodiments, the RE 108*a* and the SE 108*b* can be any precious metal, any group III, or a transition metal. In some embodiments, the RE 108*a* and the SE 108*b* can be mixtures or alloys of the above metals. In some embodiment, the SE 108*b* and the wire 118*b* are made from a conductor that does not react with the aluminum, the catalyst or the hydrogen. In some embodiments, the RE 108*a* and the wire 118*a* are a conductor that does not react with hydrogen. In some embodiments, the RE 108*a*, the SE 108*b* and the wires 112*a* and 112*b* are an n-type or p-type semiconductor. However, platinum is preferred over silver, gold and n-type or p-type semiconductors for the RE 108*a*, the SE 108*b* and the wires 112*a* and *b*. In some embodiments, the wires 112*a* and *b* can be any material used for the RE 108*a* and the SE 108*b*. Although in FIG. 1 the wire 112*a* passes through the wall of the reaction chamber 114, in another embodiment, the wire 112*b* can be attached to and run along an exterior wall of the ceramic vessel 102.

In some embodiments, the meter 116 is a multimeter. In some embodiments, the meter 116 converts the voltage between the wires 112*a* and *b* to the partial pressure of the hydrogen in the reaction chamber 114. In some embodiments, the meter 116 converts the voltage between the wires 112*a* and *b* to a concentration of the hydrogen in the reaction chamber 114. In some embodiments, the meter 116 converts the voltage between the wires 112*a* and *b* to the ratio of the partial pressures of the hydrogen in the reaction chamber 114 to the reference partial pressure. In some embodiments, the meter 116 converts the voltage between the wires 112*a* and *b* to a ratio of the concentration of the hydrogen in the reaction chamber 114 to the concentration of the hydrogen in the ceramic vessel 102.

In some embodiments, thermal sensors 118*a* and 118*b* measure the temperature of the reference gas and the reaction chamber 114, respectively. In some embodiments, a heater 120*b* heats the reaction chamber 114. In some embodiments, the heater 120*b* heats a source of starting materials of the reaction before introducing the starting materials into the reaction chamber 114. In some embodiments, the heater 120*a* is located in a reservoir 122 for the reference gas or at another location where the reference gas passes before entering the ceramic vessel 102. In some embodiments, the heater 120*a* heats the reference gas to the same temperature as the reaction chamber 114, based on temperature measurements of the thermal sensors 118*a* and 118*b*.

Figure 2:
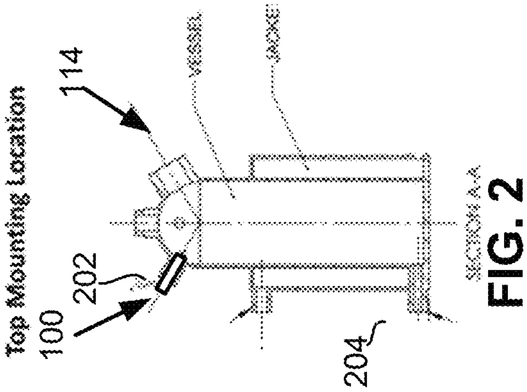
FIGS. 2 and 3 illustrate different configurations of the hydrogen sensor and the reaction chamber.
Figure 3:
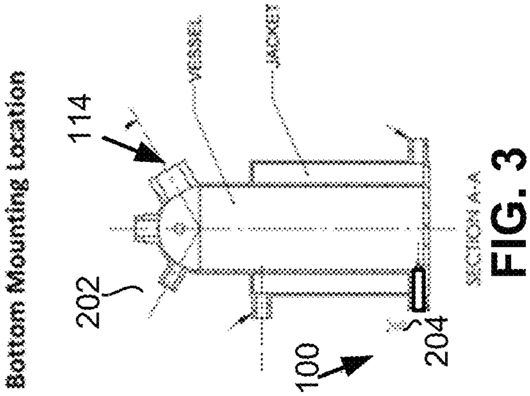

FIGS. 2 and 3 illustrate different ports on the reaction chamber 114 into which the hydrogen sensor 100 is inserted. In FIG. 2, the hydrogen sensor 100 is inserted into a port at the top of the reaction chamber 114 (a top port 202), and in FIG. 3, the hydrogen sensor 100 is inserted into a port at the bottom of the reaction chamber 114 (a bottom port 204). In some embodiments, the hydrogen sensor 100 is held in place by a binder. The other ports of the reaction chamber 114 are used for introducing the starting material for the reaction and removing the products of the reaction. In some embodiments, the starting materials are water and aluminum. In some embodiments, the starting materials include a catalyst. In some embodiments, the catalyst is one or more compounds selected from any of (or a combination of) KOH, NaOH, NaCl and KCl, which may be included in a basic solution (containing ions), having more $OH^-$ than $H^+$ ions or having a pH greater than 7).

Figure 4:
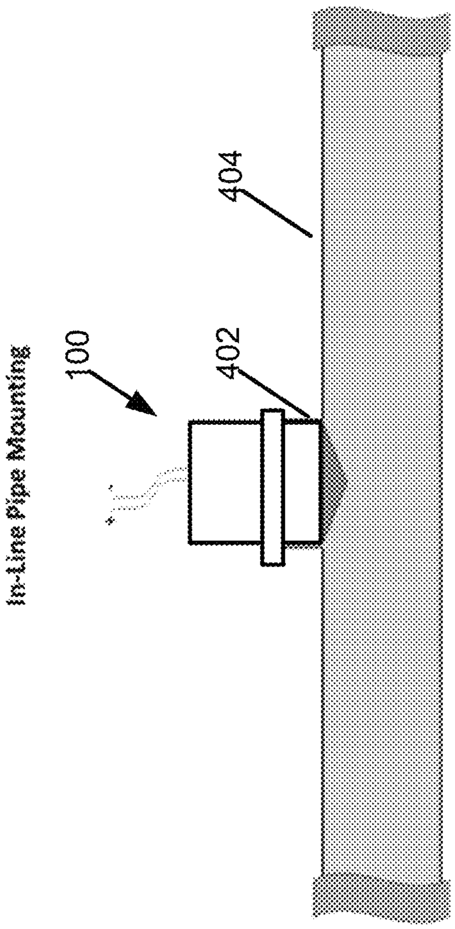
FIG. 4 illustrates an example of another type of port in which the hydrogen sensor can be inserted.

FIG. 4 illustrates an embodiment in which the hydrogen sensor 100 is inserted into a port 402 of a conduit 404. In the embodiment of FIG. 4, the port 402 is located on the conduit 404. In some embodiments, the conduit 404 is a pipe. In some embodiments, the conduit 404 carries hydrogen out of the reaction chamber 114 (and is a conduit for outgoing hydrogen), which was produced by the reaction in the reaction chamber 114. Referring to FIGS. 2-4, a high-temperature sealant or cement holds the hydrogen sensor 100 in the top port 202, the bottom port 204 or the port 402 with a high-temperature sealant or cement, which also prevents material from leaking out of the reaction chamber 114. In some embodiments, the hydrogen sensor 100 fits snuggly into the top port 202, the bottom port 204 or the port 402, to facilitate sealing any gap between the hydrogen sensor 100 and the port 402 with the high temperature cement, and thereby help prevent material from leaking out of the reaction chamber 114.

Figure 5:
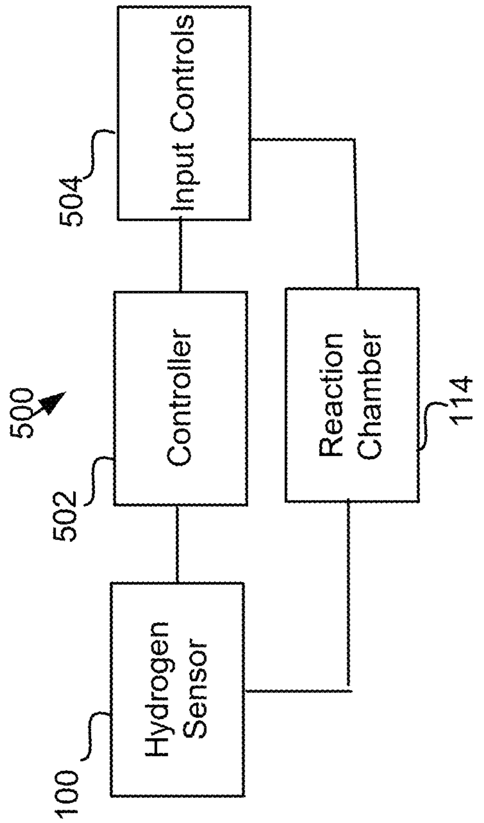
FIG. 5 illustrates a block diagram of an embodiment of a feedback system in which the hydrogen sensor is deployed.

FIG. 5 illustrates a block diagram of an embodiment of a feedback system 500 in which the hydrogen sensor 100 is used. In the feedback system 500, after the hydrogen sensor 100 produces an output (based on the ratio of the partial pressure of the hydrogen in the reaction chamber 114 to the partial pressure of the hydrogen in the ceramic vessel 102), the output is sent to a controller 502. In some embodiments, the controller 502 replaces the meter 116. Alternatively, the controller 502 is an embodiment of the meter 116. In some embodiments, the controller 502 includes a processor system and memory system, and the memory system includes program memory that stores machine instructions and working memory used for storing intermediate results of computations. The machine instructions, when implemented by the processor, cause the processor to run algorithms for performing the functions attributed to the controller 502.

The controller 502 determines whether the ratio of partial pressures is within an acceptable range of values. If the ratio of partial pressures is outside of the acceptable range of values, the controller 502 computes a corrective action and sends a signal to the input controls 504, which in turn causes the corrective action to occur within the reaction chamber 114. In some embodiments, the controller 502 is also connected to other sensors, and the corrective action is based on the ratio of partial pressures and information derived from the other sensors. In some embodiments, the other sensors include a thermal sensor, pressure gauge and pH sensor for measuring the temperature, pressure and pH, respectively, within the reaction chamber. In some embodiments, the other sensors include flow meters for measuring the flow rate of the starting materials flowing into the reaction chamber 114 and the flow rate of the end products leaving the reaction chamber 114.

In some embodiments, the input controls 504 include a temperature setting for a heater, settings for valves and pumps controlling how open the valves are and the pressures provided by the pumps. In some embodiments, the corrective action includes changing the temperature within the reaction chamber, by changing the temperature setting of the heater that heats the reaction chamber 114. In some embodiments, the corrective action includes changing a pH of a mixture of the components in the reaction chamber 114. In some embodiments, the corrective action includes adjusting a ratio of the starting material to one another. In some embodiments, the corrective action involves changing the ratio of water to the Al pure metal or alloy or recycled mixture with various particle sizes, ranging from powder to large granules to chunks. In some embodiments, the corrective action involves changing the concentration of the catalyst. In some embodiments, the temperature, pH or concentration of the catalyst are increased to increase the rate of reaction when the reaction rate is too slow, as indicated by the ratio of the hydrogen in the reaction chamber to the reference hydrogen being too low. Similarly, the temperature, pH or catalyst concentration are decreased when the reaction rate is too fast as indicated by the ratio of the hydrogen in the reaction chamber to the reference hydrogen being too high.

In some embodiments, the controller 502 receives signals from the thermal sensors 118*a* and *b* and turns on the heater 120*a* when the thermal sensors 118*a* and *b* indicate that the temperature of the reference gas is less than the reaction chamber 114.

Figure 6:
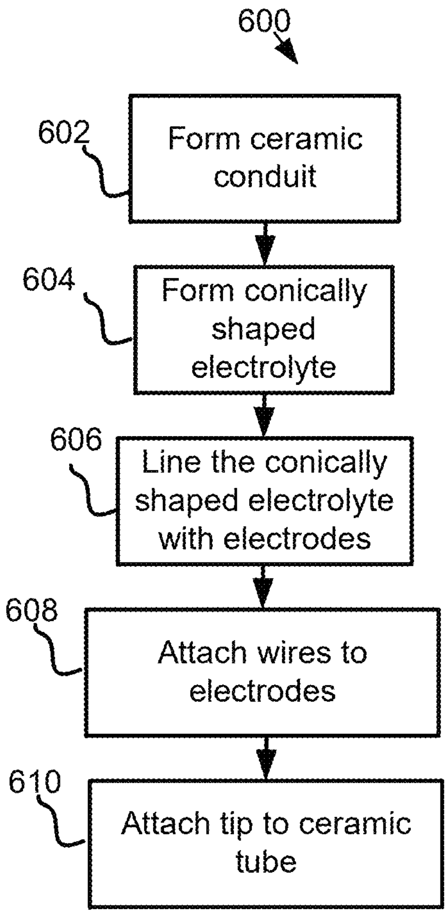
FIG. 6 illustrates a flowchart of various embodiments of a method of building the hydrogen sensor.

FIG. 6 illustrates a flowchart of some embodiments of a method 600 of building the hydrogen sensor 100. The ceramic vessel 102 is formed (step 602). In some embodiments, a mold is used to form the ceramic. The electrolyte 110 is formed into a conical shape (step 604). In some embodiments, the electrolyte material is molded in the conical shape. In some embodiments, the electrolyte is bent into the shape illustrated in FIG. 1. In some embodiments, the conical shape is a conc. In some embodiments, the walls of the cone are flat. In some embodiments, the walls of the cone are curved. The conical shape facilitates inserting the hydrogen sensor 100 into a port of the reaction chamber 114 or another port. The conical shape increases the structural strength and surface area of the SE. However, in other embodiments, the tip has other shapes. Next, the electrolyte 110 is lined with electrodes, forming the RE 108*a* and the SE 108*b* (step 606, see the discussion of the RE 108*a* and the SE 108*b* of FIG. 1), therein forming the tip of the hydrogen sensor 100. In some embodiments, the RE 108*a* and the SE 108*b* are formed by vapor depositions, or deposited atom by atom or molecule in another manner. A deposition process is used so that there are spaces between the atoms or molecules of the RE 108*a* and the SE 108*b* within which the hydrogen ions can travel. Then the wires 112*a* and 112*b* are attached to the RE 108*a* and the SE 108*b*, respectively (step 608, see the discussion of the wires 112*a* and *b* of FIG. 1). Next, the tip is attached to the ceramic vessel 102 by the binder 106 (step 610, see the discussion of FIG. 1), therein forming the hydrogen sensor 100. The steps of the method 600 can be performed in any order except that the ceramic vessel 102 and the electrolyte 110 are formed before being attached to each other by the binder 106, the electrolyte 110 is formed before being lined with the RE 108*a* and the SE 108*b*. However, the electrolyte 110 could be formed on one of, or between, the RE 108*a* and the SE 108*b*. Ordinarily, the wire 112*a* and the RE 108*a* would be constructed before being attached, and the wire 112*b* and the RE 108*b* would be constructed before being attached.

Figure 7:
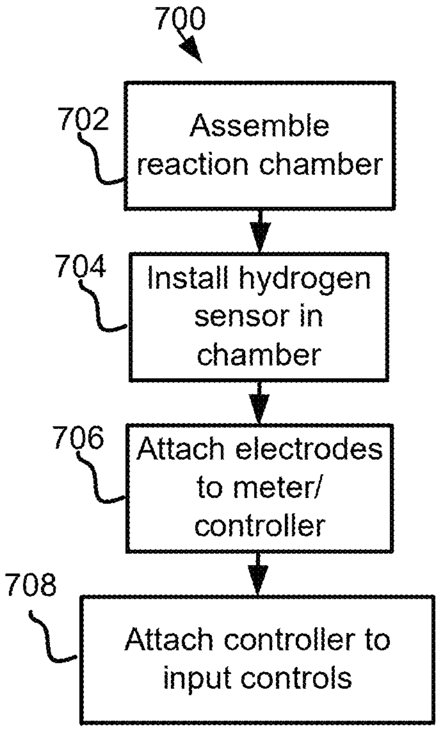
FIG. 7 illustrates a flowchart of various embodiments of a method of setting up the hydrogen sensor and system.

FIG. 7 illustrates a flowchart of various embodiments of a method 700 of setting up the hydrogen sensor 100 and system. The reaction chamber 114 and associated system is assembled (step 702), which, in some embodiments, includes assembling the input controls 504 (see the discussion of FIG. 5). Then, the hydrogen sensor 100 is inserted into one of the top port 202, the bottom port 204 or the port 402 (see the discussion of FIGS. 2-4), with the tip being inserted first, therein locating the tip within the reaction chamber 114 or within the conduit 404 (step 704). As part of the step 704, the wire 112*b* is positioned to have one end of the wire 112*b* outside the reaction chamber 114. Also, as part of the step 704, the gas inlet 104 is positioned in the ceramic vessel 102 and attached to a source of a gas that includes hydrogen (see the discussion of FIG. 1 regarding the gas inlet 104). Next, in some embodiments, the wires 112*a* and 112*b* are attached to an output, which in some embodiments is the meter 116 and in some embodiments is controller 502 (step 706). In some embodiments, the step 706 includes connecting the hydrogen sensor 100 to the meter 116 or the controller 502. Then, in embodiments including controller 502, the controller 502 is connected to the input controls 504 (step 708). The steps of the method 700 can be performed in any order or simultaneously, except that the reaction chamber 114 or the conduit 404 would be constructed before installing the hydrogen sensor 100 therein.

Figure 8:
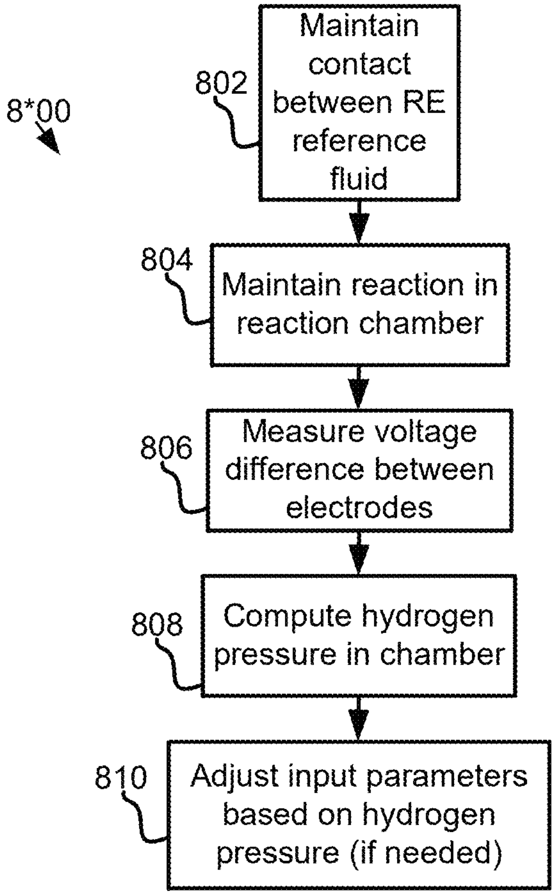
FIG. 8 illustrates a flowchart of various embodiments of a method of operating the hydrogen sensor.

FIG. 8 illustrates a flowchart of some embodiments of a method 800 of using the hydrogen sensor 100. Initially, the gas having the reference partial pressure of hydrogen gas is guided into the ceramic vessel 102 by the gas inlet 104 (step 802, see the discussion of the gas inlet 104 in FIG. 1).

Next, a reaction is maintained in the reaction chamber 114 in a steady state (step 804). In some embodiments, the step 802 involves placing the starting materials into the reaction chamber 114 and maintaining a desired set of conditions for performing the reaction within the reaction chamber 114. In some embodiments, the desired set of conditions includes a desired temperature range, pressure range, pH range and ranges of concentrations of materials. Although the hydrogen sensor 100 can measure the hydrogen concentration continually, the hydrogen sensor 100 can also be used in other situations. For example, the starting materials are placed in the reaction chamber 114, and after the reaction is finished (1) the end products are removed, (2) more starting materials are added and (3) the reaction is restarted.

Next, the voltage drop between the wires 112*a* and 112*b* is measured (step 806). Next, the partial pressure of the hydrogen in the reaction chamber 114 is determined, based on the ratio of the partial pressures of the hydrogen (step 808, see the discussion of FIG. 1 and the SE 108*a* and the RE 108*b* regarding the ratio of partial pressures). Next, if the partial pressure ratio is outside of a desired range, corrective action is taken. In some embodiments, the corrective action includes adjusting the input controls 504 based on the partial pressure of the hydrogen in the reaction chamber (step 810, see the discussion of the controller 502 and the input controls 504 of FIG. 5). In some embodiments, the corrective action is determined based on the voltage drop between the wires 112*a* and 112*b* without directly computing the partial pressure ratio. For example, in some embodiments, the corrective action is determined based on a mathematical model or lookup table that is interpolated, where the lookup table or mathematical model has (1) the voltage drop as an input parameter and (2) outputs that are indicative of corrective actions that are based on the equation 2, where the table is interpolated. The step of method 800 can be performed in any order or simultaneously.

Although the disclosed method and apparatus is described above in terms of various examples of embodiments and implementations, it should be understood that the particular features, aspects and functionality described in one or more of the individual embodiments are not limited in their applicability to the particular embodiment with which they are described. Thus, the breadth and scope of the claimed invention should not be limited by any of the examples provided in describing the above disclosed embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide examples of instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the disclosed method and apparatus may be described or claimed in the singular, the plural is contemplated to be within the scope thereof unless limitation to the singular is explicitly stated.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described with the aid of block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A system comprising a hydrogen sensor, the hydrogen sensor comprising:

a) a proton-carrying electrolyte;

b) an RE (reference electrode) lining a first side of the proton-carrying electrolyte;

c) an SE (sense electrode) lining a second side of the proton-carrying electrolyte; and d) a voltage measuring device that is electrically connected to the RE and the SE to measure a voltage drop between the RE and the SE, the proton-carrying electrolyte being capable of maintaining a gradient of concentration of hydrogen cations between the SE and the RE at 250° C.;

the system further comprising a non-transient memory and a controller, the non- transient memory storing one or more machine instructions, which when implemented cause the controller to control a rate of flow of an electrolyte and aluminum into a reaction chamber based on readings of the hydrogen sensor, the electrolyte including potassium hydroxide dissolved in water, the potassium hydroxide being a catalyst to maintain a reaction between aluminum and water.

2. The system of claim 1 wherein the proton- carrying electrolyte comprises a perovskite doped with a rare earth element.

3. The system of claim 2 wherein the perovskite includes an A cation and a B cation in a structure $ABO_3$, where the A cation is selected from any of Ca, Ba, Sr, La and K, and the B cation is selected from any of Ce, Zr, Ta and Nb.

4. The system of claim 3, wherein the A cation is a 12-coordinated $A^{2+}$ cation, and the B cation is a 6-coordinated $B^{4+}$ cation.

5. The system of claim 3, where both the A cation and the B cation are doped.

6. The system of claim 1, wherein the proton-carrying electrolyte comprises a perovskite doped with an element selected from any of Y, Yb, In, Sc, Gd, Nd, Sm, Ga, Er or combinations thereof.

7. The system of claim 1, wherein the proton-carrying electrolyte comprises a perovskite doped with a rare earth element, wherein the proton-carrying electrolyte is a barium-zirconate-cerate material doped with yttrium (BCZY).

8. The system of claim 1, further comprising a first platinum wire connecting the RE to the voltage measuring device and a second platinum wire connecting the SE to the voltage measuring device.

9. The system of claim 1, the voltage measuring device comprising a multimeter.

10. The system of claim 1, the voltage measuring device comprising a including the controller.

11. The system of claim 10, the controller including one or more machine instructions, and when the controller implements the one or more machine instructions, the controller reads the voltage drop and determines whether to take a corrective action based on an equation, $$P'_{H2} = P''_{H2} e^{\frac{-2E}{T\left(\frac{F}{R}\right)}},$$

and based on whether the $P'_{H2}$ or the E is outside of an acceptable range of values, where (1) the $P'_{H2}$ is a partial pressure of hydrogen at the SE, (2) the $P''_{H2}$ a partial pressure of hydrogen at the RE, (3) the F/R is a value of a ratio of Faraday's constant to an ideal gas' universal constant, (4) the T is a value of absolute temperature at the RE and (5) E is the potential difference between the RE and the SE.

12. The system of claim 1, the proton-carrying electrolyte having a conical shape.

13. The system of claim 1, further comprising: a ceramic vessel, which is connected to the proton-carrying electrolyte.

14. The system of claim 13, further comprising: a gas inlet which is a conduit connecting a source and a region in contact with the RE, via which a reference gas is transferable from the source to the region in contact with the RE.

15. The system of claim 13, the ceramic vessel and the proton-carrying electrolyte forming a cavity for holding a reference gas.

16. The system hydrogen sensor of claim 1 wherein the proton-carrying electrolyte comprises barium-zirconate-cerate material doped with yttrium (BCZY), having a barium zirconate site and a barium cerate site;

where both the barium zirconate site and the barium cerate site are doped;

the RE and the SE are made from platinum;

the proton-carrying electrolyte having a conical shape; and the hydrogen sensor further including at least a ceramic vessel connected to the proton-carrying electrolyte so that the ceramic vessel and the proton-carrying electrolyte form a cavity in which the RE is within the cavity and the SE is outside of the cavity.

17. A system comprising:

a) a hydrogen sensor, the hydrogen sensor including an electrolyte having a barium-zirconate-cerate material doped with yttrium (BCZY), the electrolyte having a conical shape; wherein i. the conical shape has an exterior side covered with a platinum SE (sensor electrode) and ii. the conical shape has an interior side covered with a platinum RE (reference electrode); and b) a reaction chamber, the reaction chamber including, i. one or more inlet conduits for transporting starting materials into the reaction chamber, the starting materials including aluminum and water;

ii. one or more outlet conduits for transporting an end product out of the reaction chamber, the end product including hydrogen; and iii. a port for accepting the hydrogen sensor; and c) an inlet conduit connected to a source for a reference gas for carrying the reference gas to the interior side of the conical shape, causing the reference gas to come in contact with the platinum RE;

wherein, i. the hydrogen sensor being inserted into the port of the system, with the platinum SE being oriented to face gas from the reaction chamber so that a ratio of a hydrogen partial pressure of the gas from the reaction chamber and a hydrogen partial pressure of the reference gas generates a voltage drop between the platinum SE and the platinum RE;

ii. the electrolyte being capable of maintaining a gradient of concentration of hydrogen cations between the platinum SE and the platinum RE at 250° C.;

iii. the platinum SE and the platinum RE being in electrical contact with an output; and iv. a non-transient memory and a controller, the non-transient memory storing one or more machine instructions, which when implemented cause the controller to control a rate of flow of an electrolyte and the aluminum into the reaction chamber based on readings of the hydrogen sensor, the electrolyte including potassium hydroxide dissolved in the water, the potassium hydroxide being a catalyst to maintain a reaction between the aluminum and the water.

18. The system of claim 17, the hydrogen sensor further comprising a ceramic vessel attached to the interior side of the conical shape.

19. The system of claim 17, the platinum SE being located in the reaction chamber.

20. The system of claim 17, the port for accepting the hydrogen sensor being located on one of the one or more outlet conduits, and the platinum SE being located in the one of the one or more outlet conduits.

* * * * *